United States Patent
Nakai et al.

(10) Patent No.: US 10,729,405 B2
(45) Date of Patent: Aug. 4, 2020

(54) COMPOSITION FOR ACOUSTIC WAVE PROBE, SILICONE RESIN FOR ACOUSTIC WAVE PROBE USING SAME, ACOUSTIC WAVE PROBE, ULTRASONIC PROBE, ACOUSTIC WAVE MEASUREMENT APPARATUS, ULTRASONIC DIAGNOSTIC APPARATUS, PHOTOACOUSTIC WAVE MEASUREMENT APPARATUS AND ULTRASOUND ENDOSCOPE

(71) Applicant: FUJIFILM Corporation, Tokyo (JP)

(72) Inventors: Yoshihiro Nakai, Kanagawa (JP);
Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/102,961

(22) Filed: Aug. 14, 2018

(65) Prior Publication Data
US 2018/0360416 A1    Dec. 20, 2018

Related U.S. Application Data (63) Continuation of application No. PCT/JP2017/009782, filed on Mar. 10, 2017.

(30) Foreign Application Priority Data

Mar. 25, 2016    (JP) ................................ 2016-061401

(51) Int. Cl.
*C08L 83/04* (2006.01)
*A61B 8/00* (2006.01)
(Continued)

(52) U.S. Cl.
CPC ............ *A61B 8/4281* (2013.01); *A61B 8/445* (2013.01); *A61B 8/4483* (2013.01); *C08G 77/04* (2013.01);
(Continued)

(58) Field of Classification Search
None
See application file for complete search history.

(56) References Cited

U.S. PATENT DOCUMENTS 4,335,035 A * 6/1982 Hatanaka ................ C08L 83/04
523/212
4,442,060 A * 4/1984 Bouverot ................ C08K 3/36
264/328.2
(Continued)

FOREIGN PATENT DOCUMENTS

JP    8-305375 A    11/1996
JP    2003-153902 A    5/2003
(Continued)

OTHER PUBLICATIONS

Communication dated Apr. 9, 2019 from Japanese Patent Office in counterpart JP Application No. 2018-507222.
(Continued)

*Primary Examiner* — Robert S Loewe
(74) *Attorney, Agent, or Firm* — Sughrue Mion, PLLC (57) ABSTRACT

Provided is a composition for an acoustic wave probe including a polysiloxane mixture containing polysiloxane and silica particles of which an average primary particle diameter exceeds 16 nm and less than 100 nm and which are subjected to surface treatment, and organic peroxide, and a silicone resin for an acoustic wave probe, the acoustic wave probe, an ultrasound probe, an acoustic wave measurement apparatus, an ultrasound diagnostic apparatus, a photoacoustic wave measurement apparatus, and an ultrasound endoscope using the composition for an acoustic wave probe.

17 Claims, 1 Drawing Sheet

(51) Int. Cl.
  *C08K 5/14* (2006.01)
  *C08K 9/06* (2006.01)
  *G10K 11/02* (2006.01)
  *C08G 77/04* (2006.01)
  *C08K 3/36* (2006.01)
  *C08K 7/18* (2006.01)
  *C08K 13/06* (2006.01)
  *G10K 11/30* (2006.01)
  *A61B 5/00* (2006.01)
  *A61B 8/12* (2006.01)
  *C08G 77/20* (2006.01)
  *C08G 77/00* (2006.01)

(52) U.S. Cl.
  CPC .................. *C08K 3/36* (2013.01); *C08K 5/14* (2013.01); *C08K 7/18* (2013.01); *C08K 9/06* (2013.01); *C08K 13/06* (2013.01); *C08L 83/04* (2013.01); *G10K 11/02* (2013.01); *G10K 11/30* (2013.01); *A61B 5/0095* (2013.01); *A61B 8/12* (2013.01); *C08G 77/20* (2013.01); *C08G 77/80* (2013.01); *C08K 2201/003* (2013.01); *C08K 2201/011* (2013.01)

(56) References Cited

U.S. PATENT DOCUMENTS

| | | | | | |
|---|---|---|---|---|---|
| 4,651,850 | A | * | 3/1987 | Matsuo | G10K 11/30 181/175 |
| 4,842,837 | A | * | 6/1989 | Shimizu | B82Y 30/00 423/335 |
| 4,985,477 | A | * | 1/1991 | Collins | C08K 9/06 106/490 |
| 5,013,772 | A | * | 5/1991 | Fujiki | C08K 9/06 523/209 |
| 5,028,653 | A | * | 7/1991 | Desmonceau | A61K 9/1641 523/209 |
| 5,268,396 | A | * | 12/1993 | Lai | C08F 30/08 522/28 |
| 5,691,401 | A | * | 11/1997 | Morita | C08J 3/128 523/435 |
| 5,700,853 | A | * | 12/1997 | Yoshida | C08K 3/36 523/204 |
| 5,834,110 | A | * | 11/1998 | Misawa | H01B 17/325 428/328 |
| 5,977,243 | A | * | 11/1999 | Barthel | C08G 77/045 524/588 |
| 6,011,105 | A | * | 1/2000 | Ota | C08K 3/36 524/494 |
| 6,294,635 | B1 | * | 9/2001 | Achenbach | C08K 5/0091 528/15 |
| 6,418,084 | B2 | * | 7/2002 | Saito | G10K 11/30 367/150 |
| 7,332,144 | B2 | * | 2/2008 | Konya | B82Y 30/00 106/287.13 |
| 7,563,839 | B2 | * | 7/2009 | Scholz | C08K 3/36 523/212 |
| 7,972,431 | B2 | * | 7/2011 | Meyer | C09C 1/3081 106/482 |
| 8,071,693 | B2 | * | 12/2011 | Banerjee | C08G 73/106 525/431 |
| 8,292,818 | B2 | | 10/2012 | Yamashita et al. | |
| 9,012,586 | B2 | * | 4/2015 | Yoshitake | H01L 33/56 428/447 |
| 2007/0191537 | A1 | * | 8/2007 | Meyer | B82Y 30/00 524/588 |
| 2007/0282204 | A1 | * | 12/2007 | Yamashita | G10K 11/02 600/459 |
| 2008/0312537 | A1 | * | 12/2008 | Hyuga | B06B 1/0622 600/459 |
| 2009/0243436 | A1 | | 10/2009 | Rubinsztajn et al. | |
| 2011/0112406 | A1 | | 5/2011 | Rubinsztajn et al. | |
| 2011/0257532 | A1 | * | 10/2011 | Sasaki | B06B 1/00 600/459 |
| 2012/0004555 | A1 | * | 1/2012 | Ohnuma | H01L 41/253 600/459 |
| 2012/0123054 | A1 | * | 5/2012 | Matsumoto | C08K 3/22 524/701 |
| 2013/0189887 | A1 | * | 7/2013 | Akechi | D03D 1/02 442/60 |
| 2013/0331821 | A1 | * | 12/2013 | Okada | C08L 83/04 604/525 |
| 2015/0259532 | A1 | * | 9/2015 | Hayashida | C08K 3/36 524/493 |
| 2015/0380636 | A1 | * | 12/2015 | Fujisawa | C08K 3/22 524/783 |
| 2016/0051228 | A1 | * | 2/2016 | Nakai | A61B 5/0095 |
| 2016/0122611 | A1 | * | 5/2016 | Yoshida | C08L 83/04 252/75 |
| 2016/0359092 | A1 | * | 12/2016 | Hotta | H01L 33/56 |
| 2017/0000455 | A1 | | 1/2017 | Nakai | |

FOREIGN PATENT DOCUMENTS

| | | |
|---|---|---|
| JP | 2003-180694 A | 7/2003 |
| JP | 2005-125071 A | 5/2005 |
| JP | 2009-72605 A | 4/2009 |
| JP | 2009-240782 A | 10/2009 |
| JP | 2011-72702 A | 4/2011 |
| JP | 2015-189818 A | 11/2015 |
| WO | 2015/146308 A1 | 10/2015 |

OTHER PUBLICATIONS

International Search Report dated May 23, 2017 in counterpart international application No. PCT/JP2017/009782.

Written Opinion dated May 23, 2017 in counterpart international application No. PCT/JP2017/009782.

International Preliminary Report on Patentability with translation of Written Opinion dated Sep. 25, 2018 in counterpart international application No. PCT/JP2017/009782.

Communication dated Jul. 30, 2019, from the Japanese Patent Office in counterpart application No. 2018-507222.

* cited by examiner

COMPOSITION FOR ACOUSTIC WAVE PROBE, SILICONE RESIN FOR ACOUSTIC WAVE PROBE USING SAME, ACOUSTIC WAVE PROBE, ULTRASONIC PROBE, ACOUSTIC WAVE MEASUREMENT APPARATUS, ULTRASONIC DIAGNOSTIC APPARATUS, PHOTOACOUSTIC WAVE MEASUREMENT APPARATUS AND ULTRASOUND ENDOSCOPE

CROSS-REFERENCE TO RELATED APPLICATIONS

This application is a Continuation of PCT International Application No. PCT/JP2017/009782 filed on Mar. 10, 2017, which claims priority under 35 U.S.C. § 119 (a) to Japanese Patent Application No. JP2016-061401 filed in Japan on Mar. 25, 2016. Each of the above applications is hereby expressly incorporated by reference, in its entirety, into the present application.

BACKGROUND OF THE INVENTION

1. Field of the Invention

The present invention relates to a composition for an acoustic wave probe, a silicone resin for an acoustic wave probe using the same, the acoustic wave probe, and an ultrasound probe. Furthermore, the present invention relates to an acoustic wave measurement apparatus, an ultrasound diagnostic apparatus, a photoacoustic wave measurement apparatus, and an ultrasound endoscope.

2. Description of the Related Art

In the acoustic wave measurement apparatus, an acoustic wave probe is used which irradiates a test object or a site (hereinafter, simply referred to as an object) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Acoustic waves, such as ultrasonic waves and photoacoustic waves, which have an appropriate frequency in accordance with a test object and/or measurement conditions, are selected as the acoustic waves.

For example, the ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

The acoustic wave measurement apparatus performs transmission and reception of an acoustic wave on a living body (typically, the human body) which is a test object. Therefore, it is necessary to fulfill requirements such as consistency in the acoustic impedance within the living body and/or decrease in acoustic attenuation.

For example, a probe for an ultrasound diagnostic apparatus (also referred to as an ultrasound probe) which is a kind of acoustic wave probe includes a piezoelectric element which transmits and receives an ultrasonic wave and an acoustic lens which is a portion coming into contact with a living body. An ultrasonic wave generated from the piezoelectric element is incident on the living body after being transmitted through the acoustic lens. In a case where the difference between acoustic impedance (density×acoustic velocity) of the acoustic lens and acoustic impedance of the living body is large, the ultrasonic wave is reflected by the surface of the living body. Therefore, the ultrasonic wave is not efficiently incident on the living body. For this reason, it is difficult to obtain a favorable resolution. In addition, it is desirable that ultrasonic attenuation of the acoustic lens is low in order to transmit and receive the ultrasonic wave with high sensitivity.

For this reason, a silicone resin of which the acoustic impedance is close to the acoustic impedance (in the case of a human body, $1.4 \times 10^6$ to $1.7 \times 10^6$ kg/m$^2$/sec) of a living body and which has a low ultrasonic attenuation is used as a material of the acoustic lens.

For example, JP2015-189818A discloses a composition for an ultrasound probe which contains at least three types of polyorganosiloxane mixtures containing specific branched polyorganosiloxane, and a silicone resin for an ultrasound probe obtained by vulcanizing the composition.

SUMMARY OF THE INVENTION

In JP2015-189818A, in addition to setting acoustic impedance of the silicone resin for an ultrasound probe to be within a predetermined numerical range, studies have been conducted to improve the characteristics, such as decrease in acoustic attenuation, resin hardness, and mechanical strength, required for a probe used in a living body.

The above-described characteristics are characteristics required for a silicone resin for an acoustic wave probe used in a living body. In addition to the above-described characteristics, further improvement in quality has been required for acoustic wave probes in recent years. In particular, from the viewpoint of long-term use and the necessity to withstand strong disinfectants, improvement of chemical resistance is strongly required.

In view of the above-described circumstances, an object of the present invention is to provide a composition for an acoustic wave probe in which the acoustic impedance of a silicone resin for an acoustic wave probe after cross-linking is close to an acoustic impedance value of a living body, the acoustic attenuation decreases, and the chemical resistance, the hardness and the tear strength can be improved.

In addition, another object of the present invention is to provide a silicone resin for an acoustic wave probe using the composition for an acoustic wave probe of the present invention, the acoustic wave probe, an ultrasound probe, an acoustic wave measurement apparatus, an ultrasound diagnostic apparatus, a photoacoustic wave measurement apparatus, and an ultrasound endoscope.

Furthermore, another object of the present invention is to provide a composition for an acoustic wave probe and a silicone resin for an acoustic wave probe in which it is possible to improve the sensitivity of an ultrasound probe in which capacitive micromachined ultrasonic transducers (cMUT) are used as ultrasonic diagnostic transducer arrays, the photoacoustic wave measurement apparatus, and the ultrasound endoscope.

The present inventors have conducted intensive studies on constituent materials of the acoustic wave probe. As a result, they have found that the above-described problems can be solved using a composition which contains polysiloxane, organic peroxide, and silica particles of which the average primary particle diameter is within a specific range and which are subjected to surface treatment, and have completed the present invention based on the findings.

The above-described problems are solved by the following means.

<1> A composition for an acoustic wave probe, comprising: a polysiloxane mixture containing polysiloxane and silica particles of which an average primary particle diameter exceeds 16 nm and less than 100 nm and which are subjected to surface treatment; and organic peroxide.

<2> The composition for an acoustic wave probe according to <1>, in which 25 to 70 parts by mass of the above-described silica particles subjected to surface treatment are contained in 100 parts by mass in total of the polysiloxane mixture.

<3> The composition for an acoustic wave probe according to <1> or <2>, in which the polysiloxane is vinyl group-containing polysiloxane.

<4> The composition for an acoustic wave probe according to any one of <1> to <3>, in which the silica particles subjected to surface treatment are silica particles subjected to surface treatment using a silane compound.

<5> The composition for an acoustic wave probe according to any one of <1> to <4>, in which the silica particles subjected to surface treatment are silica particles subjected to surface treatment using a trimethylsilylating agent.

<6> The composition for an acoustic wave probe according to any one of <1> to <5>, in which a methanol hydrophobicity of the silica particles subjected to surface treatment is 50 to 80 mass %.

<7> The composition for an acoustic wave probe according to any one of <1> to <6>, in which the silica particles subjected to surface treatment are truly spherical.

<8> The composition for an acoustic wave probe according to any one of <1> to <7>, in which the polysiloxane has a phenyl group.

<9> The composition for an acoustic wave probe according to any one of <1> to <8>, in which a mass average molecular weight of the polysiloxane is 20,000 to 1,000,000.

<10> The composition for an acoustic wave probe according to any one of <1> to <9>, in which a mass average molecular weight of the polysiloxane is 40,000 to 300,000.

<11> A silicone resin for an acoustic wave probe which is obtained by cross-linking the composition for an acoustic wave probe according to any one of <11> to <10>.

<12> An acoustic wave probe comprising: an acoustic lens containing the silicone resin for an acoustic wave probe according to <11>; and/or an acoustic matching layer containing the silicone resin for an acoustic wave probe according to <11>.

<13> An ultrasound probe comprising: a capacitive micromachined ultrasonic transducer as an ultrasonic transducer array; and an acoustic lens containing the silicone resin for an acoustic wave probe according to <11>.

<14> An acoustic wave measurement apparatus comprising: the acoustic wave probe according to <12>.

<15> An ultrasound diagnostic apparatus comprising: the acoustic wave probe according to <12>.

<16> A photoacoustic wave measurement apparatus comprising: an acoustic lens containing the silicone resin for an acoustic wave probe according to <11>.

<17> An ultrasound endoscope comprising: an acoustic lens containing the silicone resin for an acoustic wave probe according to <11>.

Unless otherwise specified in the description of the present invention, in a case where there are groups having a plurality of the same reference numerals as each other in general formulae representing compounds, these may be the same as or different from each other, and a group (for example, an alkyl group) specified by each group may further have a substituent. In addition, the "Si—H group" means a group having three bonds on a silicon atom, but the description of the bonds is not repeated and the notation is simplified.

In addition, in the present specification, "to" means a range including numerical values denoted before and after "to" as a lower limit value and an upper limit value.

Unless otherwise specified, the mass average molecular weight in the present specification refers to a value (in terms of polystyrene) measured through gel permeation chromatography (GPC).

In the composition for an acoustic wave probe of the present invention, the acoustic impedance of a silicone resin for an acoustic wave probe after cross-linking is close to an acoustic impedance value of a living body, the acoustic attenuation decreases, and the chemical resistance, the hardness and the tear strength can be improved.

In addition, the present invention can provide a silicone resin for an acoustic wave probe using the composition for an acoustic wave probe exhibiting the above-described excellent effect, the acoustic wave probe, an ultrasound probe, an acoustic wave measurement apparatus, an ultrasound diagnostic apparatus, a photoacoustic wave measurement apparatus, and an ultrasound endoscope.

Furthermore, the present invention can provide an ultrasound probe in which cMUT is used as an ultrasonic diagnostic transducer array, and the silicone resin for an acoustic wave probe which can improve the sensitivity of the photoacoustic wave measurement apparatus and the ultrasound endoscope.

The above-described characteristics and advantages and other characteristics and advantages of the present invention become clearer in the following descriptions with reference to the accompanying drawing.

DESCRIPTION OF THE PREFERRED EMBODIMENTS

<<Composition for Acoustic Wave Probe>>

A composition for an acoustic wave probe (hereinafter, also simply referred to as a composition) of the present invention is a composition for an acoustic wave probe including: a polysiloxane mixture containing polysiloxane (A) (hereinafter, also referred to as polyorganosiloxane (A)), silica particles (B) (hereinafter, also simply referred to as silica particles (B)) of which an average primary particle diameter exceeds 16 nm and less than 100 nm and which are subjected to surface treatment, and organic peroxide (C).

Hereinafter, the polysiloxane (A), the silica particles (B) and the organic peroxide (C) will be sequentially described in detail below.

<Polysiloxane (A)>

The polysiloxane (A) of the present invention may be any polysiloxane as long as it is millable type silicone cross-linked through a radical vulcanization reaction with the organic peroxide (C).

Here, the millable type silicone is similar to unvulcanized compounded rubber of natural rubber or ordinary synthetic rubber before cross-linking, and is a general term in which it is possible to perform plasticizing or mixing using a kneading roll machine, a closed mixer, and the like. The millable type silicone is distinguished from a liquid silicone of which the state before cross-linking is a paste or liquid state.

Hereinafter, specific millable type silicone will be described using linear polysiloxane and branched polysiloxane as examples.

The polysiloxane (A) is not limited to polysiloxane described below, but may be, for example, linear polysiloxane having a partially branched structure.

[Linear Polysiloxane]

Examples of linear polysiloxane include those represented by General Formula (A1).

(A1)

In the General Formula (A1), $R^{a1}$'s each independently represent a hydrogen atom, an alkyl group, a cycloalkyl group, an alkenyl group or an aryl group, and $R^{a2}$ and $R^{a3}$ each independently represent a hydrogen atom, an alkyl group, a cycloalkyl group, an alkenyl group, an aryl group, or —O—Si($R^{a5}$)$_2$($R^{a4}$). $R^{a4}$ and $R^{a5}$ each independently represent a hydrogen atom, an alkyl group, a cycloalkyl group, an alkenyl group, or an aryl group. x1 and x2 each independently represent an integer of 1 or more. Here, a plurality of $R^{a1}$'s, a plurality of $R^{a2}$'s, a plurality of $R^{a3}$'s, and a plurality of $R^{a5}$'s may be the same as or different from each other. In addition, in a case where there are a plurality of $R^{a4}$'s, the plurality of $R^{a4}$'s may be the same as or different from each other.

Each of the groups of $R^{a1}$ to $R^{a5}$ may further be substituted with a substituent.

The number of carbon atoms in an alkyl group in $R^{a1}$ to $R^{a5}$ is preferably 1 to 10, more preferably 1 to 4, still more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a1}$ and $R^{a5}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a1}$ to $R^{a5}$ is preferably 2 to 10, more preferably 2 to 4, and still more preferably 2. Examples of the alkenyl group include a vinyl group, an allyl group, and a butenyl group.

The number of carbon atoms in an aryl group in $R^{a1}$ to $R^{5a}$ is preferably 6 to 12, more preferably 6 to 10, still more preferably 6 or 8, and particularly preferably 6. Examples of the aryl group include a phenyl group, a tolyl group, and a naphthyl group.

The alkyl group, the cycloalkyl group, the alkenyl group, and the aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a1}$ is preferably an alkyl group or an alkenyl group, more preferably an alkyl group or a vinyl group having 1 to 4 carbon atoms, and still more preferably a methyl group or a vinyl group, and particularly preferably a vinyl group. It is most preferable that both of the two $R^{a1}$'s are vinyl groups.

$R^{a2}$ is preferably an alkyl group, an alkenyl group, or an aryl group, more preferably an alkyl group having 1 to 4 carbon atoms, a vinyl group, or a phenyl group, still more preferably a methyl group or a vinyl group, and particularly preferably a methyl group.

$R^{a3}$ is preferably an alkyl group, an alkenyl group, or an aryl group, more preferably an alkyl group having 1 to 4 carbon atoms, a vinyl group, or a phenyl group, still more preferably a methyl group or a phenyl group, and particularly preferably a phenyl group.

The group represented by —O—Si($R^{a5}$)$_2$($R^{a4}$) is preferably —O—Si(CH$_3$)$_2$(CH=CH$_2$).

x1 is preferably an integer of 200 to 10,000 and more preferably an integer of 400 to 4,000.

x2 is preferably an integer of 1 to 2,500 and more preferably an integer of 40 to 1,000.

In the present invention, each of the repeating units "—Si($R^{a2}$)$_2$—O—" and "—Si($R^{a3}$)$_2$—O—" in General Formula (A1) may exist in a block-polymerized form or may be in a form in which the repeating units exist randomly.

In particular, in order to achieve both high hardness and high tear strength, linear polysiloxane having one or more vinyl groups in a molecular chain is preferable and linear polysiloxane having two or more vinyl groups in a molecular chain is more preferable.

Examples of polysiloxane having a vinyl group include polysiloxane having vinyl groups at least at a terminal of a molecular chain, or polysiloxane having at least one vinyl group or —O—Si(CH$_3$)$_2$(CH=CH$_2$) in a molecular chain.

Among them, polysiloxane having a vinyl group at least at a terminal of a molecular chain is preferable and polysiloxane having vinyl groups at least at both terminals of a molecular chain is more preferable.

The content of the vinyl group in a case where the polysiloxane (A) has a vinyl group is not particularly limited. The content of the vinyl group is, for example, 0.01 to 5 mol % and preferably 0.05 to 2 mol % from the viewpoint of forming a sufficient network using organic peroxide (C).

Here, the content of the vinyl group is represented by mol % of the vinyl group-containing siloxane unit based on 100 mol % of all the units constituting the polysiloxane (A). One vinyl group-containing siloxane unit has 1 to 3 vinyl groups. Among them, one vinyl group is preferable for one vinyl group-containing siloxane unit. For example, in a case where all Si atoms of Si in a Si—O unit and at a terminal which constitute a main chain have at least one vinyl group, the content becomes 100 mol %.

In addition, the polysiloxane (A) preferably has a phenyl group from the viewpoints of making the acoustic impedance closer to an acoustic impedance value of a living body by increasing the acoustic velocity, and increasing the hardness and the specific gravity. The content of the phenyl group in the polysiloxane (A) is not particularly limited. The content of the phenyl group is, for example, preferably 1 to 80 mol % and preferably 2 to 40 mol % from the viewpoint of mechanical strength in a case where a silicone resin for an acoustic wave probe is made.

The content of the phenyl group is represented by mol % of the phenyl group-containing siloxane unit based on 100 mol % of all the units constituting the polysiloxane (A). One phenyl group-containing siloxane unit has 1 to 3 phenyl groups. Among them, two phenyl groups are preferable for one phenyl group-containing siloxane unit. For example, in a case where all Si atoms of Si in a Si—O unit and at a terminal which constitute a main chain have at least one phenyl group, the content becomes 100 mol %.

The "unit" of polysiloxane refers to Si atoms in a Si—O unit and at a terminal which constitute a main chain.

The degree of polymerization and the specific gravity are not particularly limited. The degree of polymerization is preferably 200 to 10,000 and more preferably 400 to 4,000, and the specific gravity is preferably 0.9 to 1.1 from the viewpoint of improving the mechanical characteristics, the hardness, the chemical stability, and the like of an obtained silicone resin for an acoustic wave probe (hereinafter, also simply referred to as a silicone resin).

The kinematic viscosity at 25° C. is preferably $1 \times 10^{-5}$ to 1,000 $m^2/s$, more preferably $1 \times 10^{-4}$ to 100 $m^2/s$, and still more preferably $1 \times 10^{-3}$ to 50 $m^2/s$.

Examples of the polysiloxane having vinyl groups at least at both terminals of a molecular chain include DMS series (for example, DMS-V31, DMS-V31S15, DMS-V33, DMS-35, DMS-35R, DMS-V41, DMS-V42, DMS-V46, DMS-V51, and DMS-V52) which are trade names manufactured by GELEST, INC., and PDV series (for example, PDV-0341, PDV-0346, PDV-0535, PDV-0541, PDV-01631, PDV-01635, PDV-01641, and PDV-2335, PMV-9925, PVV-3522, FMV-4031, and EDV-2022) which are trade names manufactured by GELEST, INC.

In the DMS-V31S15, fumed silica is formulated into DMS-V31S15 in advance, and therefore, kneading using a special device is unnecessary.

[Branched Polysiloxane]

Examples of branched polysiloxane include those represented by General Formula (A2).

$(R^5)$. $R^5$ and $R^6$ each independently represent a hydrogen atom, an alkyl group, a cycloalkyl group, an alkenyl group, or an aryl group. m represents an integer of 1 or more and n represents an integer of 0 or 1 to 5. Here, a plurality of $R^1$'s, a plurality of $R^2$'s, a plurality of $R^3$'s, a plurality of $R^4$'s, a plurality of $R^6$'s, and a plurality of m's may be the same as or different from each other. In addition, in a case where there are a plurality of $R^{a5}$'s, the plurality of $R^{a5}$'s may be the same as or different from each other.

Each of the groups of $R^1$ to $R^6$ may further be substituted with a substituent.

In General Formula (A2), polysiloxane in which n is 0 can be represented by General Formula (a2).

(a2)

In General Formula (a2), $R^1$ to $R^4$ each independently represent a hydrogen atom, an alkyl group, a cycloalkyl group, an alkenyl group, an aryl group, or —O—Si$(R^6)_2$ $(R^5)$. $R^5$ and $R^6$ each independently represent a hydrogen atom, an alkyl group, a cycloalkyl group, an alkenyl group, or an aryl group. m represents an integer of 1 or more. Here, a plurality of $R^2$'s, a plurality of $R^3$'s, a plurality of $R^4$'s, a plurality of $R^6$'s, and a plurality of m's may be the same as or different from each other. In addition, in a case where there are a plurality of $R^5$'s, the plurality of $R^5$'s may be the same as or different from each other.

Each of the groups of $R^1$ to $R^6$ may further be substituted with a substituent.

In General Formulae (A2) and (a2), the above-described groups in $R^1$ to $R^6$ are synonymous with the corresponding groups in $R^{a2}$ to $R^{a5}$ in General Formula (A1), and preferred ranges are also the same as those of the corresponding groups.

(A2)

In General Formula (A2), $R^1$ to $R^4$ each independently represent a hydrogen atom, an alkyl group, a cycloalkyl group, an alkenyl group, an aryl group, or —O—Si$(R^6)_2$ At least two of a plurality of $R^1$'s and $R^4$'s are preferably vinyl groups, and at least two of the plurality of $R^4$'s are more preferably vinyl groups.

n, m, and the mass average molecular weight in General Formulae (A2) and (a2) are not particularly limited, and millable type silicone of which the kinematic viscosity at 25° C. is raw rubbery may be used.

The specific value of the kinematic viscosity is the same as that of the preferred range of the kinematic viscosity described for linear polysiloxane.

The mass average molecular weight of the polysiloxane is preferably 20,000 to 1,000,000, more preferably 40,000 to 300,000, and still more preferably 45,000 to 250,000 from the viewpoints of the mechanical strength, the hardness, and easiness of processing.

The mass average molecular weight can be measured using, for example, TOLUENE (manufactured by Shonan Wako Junyaku K.K.) as an eluent, TSKgel (registered trademark), G3000HXL (trade name)+TSKgel (registered trademark), and G2000HXL (trade name) as columns, and a RI detector under the conditions of a temperature of 23° C. and a flow rate of 1 mL/min after preparing a GPC apparatus HLC-8220 (trade name, manufactured by TOSOH CORPORATION).

The polysiloxane (A) of the present invention may be used singly or in a combination of two or more thereof. Two or less types are preferable, and one type alone is more preferable.

<Silica Particles (B)>

The silica particles (B) used in the present invention are silica particles of which an average primary particle diameter exceeds 16 nm and less than 100 nm and which are subjected to surface treatment.

The content of silica particles in 100 parts by mass in total of the polysiloxane mixture is preferably 25 to 70 parts by mass, more preferably 30 to 60 parts by mass, and still more preferably 35 to 50 parts by mass. In a case where the content of the silica particles is within the above-described ranges, the tear strength, the bending durability, and the acoustic sensitivity increase.

An effect of improving the acoustic impedance, the hardness, and the mechanical strength of a silicone resin is obtained by adding silica particles to the silicone resin. However, the acoustic attenuation increases with an increase in the amount of the silica particles added, and in a case where the addition amount is too large, the viscosity of the composition for an acoustic wave probe before cross-linking increases.

However, in the present invention, it is considered that, in a case where the silica particles (B) subjected to surface treatment which have a particle diameter within a specific range are used, it is possible to reduce the acoustic attenuation and reduce the viscosity before cross-linking. The reason for this is not yet certain, but it is presumed as follows.

That is, in a case where silica particles having a small average primary particle diameter are used, the tear strength of the silicone resin is improved and increase in the acoustic attenuation is suppressed, whereas the viscosity of the composition for an acoustic wave probe before cross-linking increases. In the present invention, by subjecting surface treatment on silica particles having an average primary particle diameter within the above-described specific range, an interaction with polysiloxane becomes stronger and the affinity increases. For this reason, it is considered that aggregation of silica particles having a small average primary particle diameter is suppressed, the viscosity of the composition for an acoustic wave probe before cross-linking is suppressed, the tear strength of the silicone resin after cross-linking is high, and the acoustic attenuation is decreased.

The average primary particle diameter of the silica particles (B) used in the present invention is greater than 16 nm and less than 100 nm, preferably 18 nm to 90 nm, more preferably 20 nm to 80 nm, and still more preferably 25 nm to 70 nm from the viewpoints of suppressing increase in the viscosity of the composition for an acoustic wave probe before cross-linking, suppressing increase in the acoustic attenuation of the silicone resin, and improving the tear strength.

Here, the average primary particle diameter means a volume average particle diameter. The volume average particle diameter can be obtained by, for example, measuring the particle diameter distribution using a laser diffraction scattering type particle diameter distribution measurement apparatus (for example, trade name "LA910" manufactured by HORIBA. Ltd.). In the present specification, for silica particles of which the average primary particle diameter has not been disclosed in the catalog or for silica particles newly manufactured, the average primary particle diameter is obtained through the above-described measurement method.

Here, the average primary particle diameter of the silica particles (B) means an average primary particle diameter in a state in which the surface treatment has been performed.

The silica particles (B) may be used singly or in a combination of two or more thereof.

The specific surface area of the silica particles (B) used in the present invention is preferably 1 to 400 $m^2/g$, more preferably 5 to 200 $m^2/g$, and particularly preferably 10 to 100 $m^2/g$ from the viewpoint of improving the hardness and/or the mechanical strength of a silicone resin to be obtained.

The silica particles (B) used in the present invention are silica particles whose surface has been treated, and preferably silica particles subjected to surface treatment with a silane compound. By treating the surfaces of silica particles using a silane compound, interaction with the polysiloxane (A) component in the silicone resin becomes stronger and affinity to the polysiloxane (A) component in the silicone resin becomes higher. Therefore, it is considered that it is possible to finely disperse silica particles. For this reason, the silica particles more favorably exhibit functions as stoppers of minute cracks generated in a case where mechanical stress is applied, and therefore, it is considered that the hardness and the mechanical strength of the silicone resin are improved.

A usual technique may be used as a technique of the surface treatment. Examples of the technique of the surface treatment using a silane compound include a technique of performing surface treatment chemically using a silane coupling agent and a technique of performing coating using a silicone compound.

(i) Silane Coupling Agent

A silane coupling agent having a hydrolyzable group is preferable as a silane coupling agent from the viewpoint of improving the hardness and/or the mechanical strength of a silicone resin. Surface modification of silica particles is performed such that a hydrolyzable group in a silane coupling agent becomes a hydroxyl group after being hydrolyzed using water and this hydroxyl group is subjected to a dehydration and condensation reaction with a hydroxyl group on the surfaces of the silica particles, thereby improving the hardness and/or the mechanical strength of an obtained silicone resin. Examples of the hydrolyzable group include an alkoxy group, an acyloxy group, and a halogen atom.

In a case where the surfaces of silica particles are hydrophobically modified, affinity between the silica particles (B) and the polysiloxane (A) becomes favorable, and therefore, the hardness and the mechanical strength of an obtained silicone resin are improved, which is preferable.

Examples of a silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyl triethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinyl methyldichlorosilane; and divinyltetramethyldisilazane.

Silica particles treated with a trialkylsilylating agent are preferable and silica particles treated with a trimethylsilylating agent are more preferable as the silica particles (B) subjected to surface treatment with a silane coupling agent since the viscosity of the polysiloxane mixture decreases and the acoustic attenuation coefficient decreases.

Examples of the silane compound include the above-described silane coupling agents and a silane coupling agent in which a functional group in a silane coupling agent is substituted with an alkyl group.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane which are silane coupling agents in which a functional group is substituted with an alkyl group.

Examples of a commercially available silane coupling agent include hexamethyldisilazane (HMDS) (trade name: HEXAMETHYLDISILAZANE (SIH6110.1), manufactured by GELEST, INC.).

A hydroxyl group existing on the surfaces of silica particles is covered with a trimethylsilyl group through a reaction with hexamethyldisilazane (HMDS), methyltrimethoxysilane (MTMS), trimethylmethoxysilane, and the like and the surfaces of the silica particles are hydrophobically modified.

In the present invention, the silane coupling agent may be used alone or in a combination of two or more thereof.

(ii) Silicone Compound

A silicone compound with which the silica particles (B) are coated may be a polymer formed through siloxane bonding.

Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group and/or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated); and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane-dimethylsiloxane terpolymer.

In addition, examples of modified silicone into which an organic group is introduced include reactive silicone into which an amino group, an epoxy group, a methoxy group, a (meth)acryloyl group, a phenoxy group, a carboxylic anhydride group (—C(=O)—O—C(=O)—R (R represents, for example, a substituent such as an alkyl group)), a hydroxy group, a sulfanyl group, a carboxyl group, and/or an organic group of a hydrogen atom are introduced; and non-reactive silicone modified with polyether, aralkyl, fluoroalkyl, long chain alkyl, long chain aralkyl, higher fatty acid ester, higher fatty acid amide, and/or polyether methoxy.

Silica particles coated with a silicone compound can be obtained through a usual method. For example, the silica particles can be obtained by being mixed and stirred in dimethylpolysiloxane for a certain period of time at 50° C. to 150° C. and being filtered.

In addition, in a case of using reactive modified silicone as a silicone compound, surface modification of silica particles is performed through reaction of an organic group with a hydroxyl group of the surfaces of the silica particles, and therefore, the hardness and/or the mechanical strength of an obtained silicone resin is improved.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

The degree of surface modification of the silica particles (B), that is, the hydrophobicity of the silica particles (B) can be examined by the following methanol hydrophobicity.

The methanol hydrophobicity of the silica particles (B) which is calculated through the following methanol titration test is preferably 40 to 80 mass %, more preferably 50 to 80 mass %, and still more preferably 60 to 80 mass %. Here, the larger the methanol hydrophobicity, the higher the hydrophobicity, and the smaller the methanol hydrophobicity, the higher the hydrophilicity.

50 ml of ion exchange water and 0.2 g of silica particles as samples are placed in a beaker at 25° C. and stirred with a magnetic stirrer, methanol is added dropwise thereto from a burette, and the amount (Xg) of methanol added dropwise until the whole sample settles is measured. The methanol hydrophobicity is calculated using the following equation.

Methanol hydrophobicity(mass %)=($X$/(50+$X$))×100

In a case where the methanol hydrophobicity is within the above-described preferred ranges, it is possible to suppress decrease in acoustic sensitivity in a case where a silicone resin for an acoustic wave probe is obtained without increase in the viscosity of the composition for an acoustic wave probe before cross-linking.

The silica particles (B) are preferably spherical.

The Wardell's sphericity of a primary particle of the silica particles (B) is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are observed using the SEM photograph, and each sphericity thereof is calculated. An average value obtained by dividing the total of the calculated sphericities by the number of observed primary particles is regarded as the sphericity.

In a case where the Wardell's sphericity is within the above-described preferred ranges, it is considered that the acoustic sensitivity is improved because the area of the acoustic wave hitting the silica particles becomes smaller in a case where the silicone resin is irradiated with the acoustic wave. In particular, it is considered that the acoustic sensitivity is more effectively improved in a case where the shapes of the silica particles (B) are truly spherical within a specific range of the average primary particle diameter of the silica particles (B) of the present invention.

In this specification, the "true spherical shape" also includes a slightly distorted sphere of which the Wardell's sphericity is within a range of 0.9 to 1.

The silica particles are roughly classified into combustion method silica (that is, funed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane depending on its production method.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3{}_3SiO_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP2007-99582A and JP2014-114175A.

<Organic Peroxide (C)>

Examples of the organic peroxide (C) of the present invention include commonly used organic peroxides such as hydroperoxide, dialkyl peroxide, peroxy ester, diacyl peroxide, peroxydicarbonate, peroxy ketal, and ketone peroxide, which have an —O—O— bond in a molecule.

Specific examples of the organic peroxide include the following organic peroxides.

Hydroperoxide: p-menthane hydroperoxide, diisopropylbenzene hydroperoxide, 1,1,3,3-tetramethylbutyl hydroperoxide, cumene hydroperoxide, t-butyl hydroperoxide, and the like.

Dialkyl peroxide: bis(2,4-dichlorobenzoyl) peroxide, bis (4-chlorobenzoyl) peroxide, bis(2-methylbenzoyl) peroxide, bis(2-t-butyl peroxy isopropyl) benzene, dicumyl peroxide, 2,5-dimethyl-2,5-bis(t-butyl peroxy) hexane, t-butyl cumyl peroxide, di-t-hexyl peroxide, di-t-butyl peroxide, 2,5-bis(t-butyl peroxy)-2,5-dimethyl-3-hexyne, and the like.

Peroxy ester: t-butyl peroxybenzoate, cumyl peroxyneodecanoate, 1,1,3,3-tetramethylbutyl peroxyneodecanoate, t-hexyl peroxyneodecanoate, t-butyl peroxyneodecanoate, t-butyl peroxyneoheptanoate, t-hexyl peroxypivalate, 1,1,3, 3-tetramethylbutyl peroxy-2-ethylhexanoate, 2,5-bis (2-ethylhexyl peroxy)-2,5-dimethylhexane, t-hexyl peroxy-2-ethyl hexanoate, t-butyl peroxymaleate, t-butyl peroxy-3,5, 5-trimethyl hexanoate, t-butyl peroxylaurate, t-butyl peroxy isopropyl monocarbonate, t-butyl peroxy-2-ethylhexyl monocarbonate, t-hexyl peroxybenzoate, 2,5-bis(benzoyl peroxy)-2,5-dimethylhexane, t-butyl peroxyacetate, t-butyl peroxy-3-methyl benzoate, and the like.

Diacyl peroxide: diisobutyryl peroxide, bis(3,5,5-trimethylhexanoyl) peroxide, dilauroyl peroxide, bis(3-carboxy propionyl) peroxide, bis(3-methylbenzoyl) peroxide, benzoyl(3-methylbenzoyl) peroxide, dibenzoyl peroxide, bis(4-methylbenzoyl) peroxide, 1,6-hexanediol-bis(t-butyl peroxycarbonate), and the like.

Peroxydicarbonate: di-n-propyl peroxydicarbonate, diisopropyl peroxydicarbonate, bis(4-t-butyl cyclohexyl) peroxydicarbonate, bis(2-ethylhexyl) peroxydicarbonate, di-sec-butyl peroxydicarbonate, and the like.

Peroxy ketal: 1,1-bis(t-hexyl peroxy)-3,3,5-trimethylcyclohexane, 1,1-bis (t-hexyl peroxy) cyclohexane, 1,1-bis(t-butyl peroxy)-2-methylcyclohexane, 1,1-bis(t-butyl peroxy) cyclohexane, 2,2-bis (t-butyl peroxy) butane, n-butyl 4,4-bis(t-butyl peroxy) valerate, 2,2-bis(4,4-bis(t-butyl peroxy) cyclohexyl) propane, and the like.

Ketone peroxide: methyl ethyl ketone peroxide, cyclohexanone peroxide, acetylacetone peroxide, and the like.

Among these organic peroxides, those having a 10-hour half-life decomposition temperature of 100° C. to 120° C. are preferable from the viewpoint of suitability of the half-life decomposition temperature for the processing temperature. Specifically, dicumyl peroxide, 2,5-dimethyl-2,5-bis(t-butylperoxy) hexane, t-butyl cumyl peroxide, di-t-hexyl peroxide, bis(2-t-butyl peroxy isopropyl) benzene, t-butyl peroxybenzoate, 2,5-bis(benzoyl peroxy)-2,5-dimethylhexane, t-butyl peroxyacetate, 2,2-bis(t-butylperoxy) butane or n-butyl 4,4-bis(t-butylperoxy) valerate are preferable.

The organic peroxides may be used alone or in combination of two or more thereof.

The content of the organic peroxide (C) with respect to 100 parts by mass of the polysiloxane (A) component is preferably 0.1 to 15 parts by mass and more preferably 0.2 to 10 parts by mass.

In a case where the amount of the organic peroxide added is within the above-described ranges, the crosslinking reaction progresses sufficiently, and decrease in hardness of a silicone resin or insufficient rubber strength and deterioration of physical properties such as increase in permanent compression distortion are suppressed. In addition, it is economically preferable, and generation of decomposition products of a cross-linking agent is suppressed. Therefore, the deterioration of physical properties such as increase in permanent compression distortion and discoloration of an obtained silicone resin sheet is suppressed.

<Other Components>

In the composition for an acoustic wave probe of the present invention, it is possible to appropriately formulate a cross-linking retardant for an addition polymerization reaction, a solvent, a dispersant, a pigment, a dye, an antistatic agent, an antioxidant, a flame retardant, and/or a thermal conductivity enhancer in addition to the polysiloxane (A), the silica particles (B), and the organic peroxide (C).

—Cross-Linking Retardant—

The cross-linking retardant is used for delaying a radical addition reaction due to organic peroxide and examples thereof include a low molecular weight vinylmethylsiloxane homopolymer (trade name: VMS-005 manufactured by GELEST, INC.).

The cross-linking rate, that is, the working time can be adjusted depending on the content of the cross-linking retardant.

[Viscosity of Composition for Acoustic Wave Probe Before Cross-Linking]

The viscosity of the composition for an acoustic wave probe before performing a crosslinking reaction is preferably low. In a case where the viscosity is too high, it becomes difficult to prepare a composition for an acoustic wave probe in which the silica particles (B) are dispersed through kneading. The viscosity of the composition for an acoustic wave probe before adding a catalyst which initiates the vulcanization reaction is measured in order to measure the viscosity before vulcanizing. Specifically, the viscosity can be measured under the following conditions.

The viscosity of the composition for an acoustic wave probe before addition of organic peroxide is measured using a viscosity/viscoelasticity measurement apparatus (for example, trade name "RheoStress RS6000" manufactured by HAAKE) under the conditions of a temperature of 23° C. and a shear rate of $0.001$ s$^{-1}$.

The viscosity (at 23° C.) measured under the above-described conditions is preferably less than or equal to 1,000,000 Pa·s, more preferably less than or equal to 500,000 Pa·s, and particularly preferably less than or equal to 100,000 Pa·s. The practical lower limit value is greater than or equal to 10 Pa·s.

In a case where the viscosity is within the above-described preferred ranges, the composition for an acoustic wave probe can be easily handled during processing. In addition, since residual air bubbles in the composition for an acoustic wave probe can be suppressed, an increase in acoustic attenuation caused by air bubbles in the silicone resin for an acoustic wave probe can also be suppressed.

<Method for Producing Composition for Acoustic Wave Probe and Silicone Resin for Acoustic Wave Probe>

The composition for an acoustic wave probe of the present invention can be prepared through usual method.

For example, the composition for an acoustic wave probe can be obtained by kneading components constituting the composition for an acoustic wave probe using a kneader, a pressure kneader, a Banbury mixer (continuous kneader), a kneading device with two rolls, and the like.

In order to prevent decomposition of organic peroxide, it is preferable that the composition for an acoustic wave probe of the present invention is stored under the condition of a temperature lower than or equal to 50° C. and preferably a temperature lower than or equal to 35° C., before use.

From the viewpoint of obtaining a homogeneous composition for an acoustic wave probe, it is preferable to first disperse the silica particles (B) in the polysiloxane (A) and then add the organic peroxide (C) thereto.

In a case where the composition for an acoustic wave probe of the present invention further contains other materials in addition to the polysiloxane (A), the silica particles (B), and the organic peroxide (C), the organic peroxide (C) is preferably added to the composition for an acoustic wave probe after obtaining a mixture in which the silica particles (B) and other materials are dispersed in the polysiloxane (A).

It is possible to obtain a silicone resin for an acoustic wave probe which is vulcanized to a desired degree by cross-linking the composition for an acoustic wave probe of the present invention. That is, the silicone resin for an acoustic wave probe of the present invention can be produced by adding organic peroxide (C) to a polysiloxane mixture containing at least polysiloxane (A) and silica particles (B) to obtain a composition for an acoustic wave probe of the present invention and then cross-linking the composition for an acoustic wave probe. Each component can be kneaded through the above-described method.

Specifically, a silicone resin for an acoustic wave probe can be obtained by, for example, heating and cross-linking the composition for an acoustic wave probe of the present invention obtained through the above-described method at 50° C. to 180° C. for 5 minutes to 240 minutes, and if necessary, further performing secondary cross-linking at 100° C. to 220° C. for 1 to 5 hours.

In particular, since the organic peroxide (C) is used in the present invention, the secondary cross-linking performed through reheating contributes to heating and removing of a decomposition product of the organic peroxide (C) and stabilizing of the characteristics of the silicone resin for an acoustic wave probe.

<Mechanical Strength and Acoustic Characteristics of Silicone Resin>

The silicone resin for an acoustic wave probe of the present invention is obtained by cross-linking the composition for an acoustic wave probe of the present invention.

Hereinafter, the mechanical strength and the acoustic characteristics of a silicone resin will be described in detail.

Here, ultrasonic characteristics among the acoustic characteristics will be described. However, the acoustic characteristics are not limited to the ultrasonic characteristics, and relates to acoustic characteristics at an appropriate frequency which is selected in accordance with a test object, measurement conditions, and the like.

[Hardness]

The hardness is preferably greater than or equal to 15, more preferably greater than or equal to 25, and still more preferably greater than or equal to 40 from the viewpoint of preventing deformation in a case where the silicone resin sheet is incorporated into an acoustic wave probe as a part of the acoustic wave probe. A practical upper limit value is less than or equal to 90. The hardness can be measured through the method described in the section of the examples.

[Tear Strength]

The tear strength is preferably greater than or equal to 7 N/cm and more preferably greater than or equal to 10 N/cm. A practical upper limit value is less than or equal to 150 N/cm. The tear strength can be measured through the method described in the section of the examples.

[Chemical Resistance]

The chemical resistance can be evaluated by measuring the IPA swelling degree in the section of the examples. The lower the IPA swelling degree is, the better the chemical resistance is. The IPA swelling degree is preferably less than or equal to 10%, more preferably less than or equal to 9%, and particularly preferably less than or equal to 8%. The practical lower limit value is greater than or equal to 1%.

[Acoustic Impedance]

The acoustic impedance is preferably within a range of $1.4 \times 10^6$ to $1.7 \times 10^6$ kg/m$^2$/sec, or a value close to this numerical range.

The acoustic impedance of a silicone resin can be obtained through the measurement method described in the section of examples.

[Acoustic (Ultrasonic) Attenuation and Sensitivity]

The acoustic (ultrasonic) attenuation and sensitivity can be measured through the method described in the section of the examples.

In an evaluation system in the present invention, the acoustic (ultrasonic) sensitivity is preferably greater than or equal to −70.0 dB.

The composition for an acoustic wave probe of the present invention is useful for medical members and can preferably be used, for example, in an acoustic wave probe or an acoustic wave measurement apparatus. The acoustic wave measurement apparatus of the present invention is not limited to an ultrasound diagnostic apparatus or a photoacoustic wave measurement apparatus, and is referred to as an apparatus that receives an acoustic wave which has been reflected or generated from an object and displays the received acoustic wave as an image or a signal strength.

Particularly, the composition for an acoustic wave probe of the present invention can suitably be used in: a material of an acoustic matching layer which is provided in an acoustic lens of an ultrasound diagnostic apparatus or between a piezoelectric element and the acoustic lens and plays a role of matching acoustic impedance between the piezoelectric element and the acoustic lens; a material of an acoustic lens in a photoacoustic wave measurement apparatus or an ultrasound endoscope; and a material or the like of an acoustic lens in an ultrasound probe including capacitive micromachined ultrasonic transducers (cMUT) as an ultrasonic transducer array.

Specifically, the silicone resin for an acoustic wave probe of the present invention is preferably applied to, for example, an ultrasound diagnostic apparatus disclosed in JP2005-253751A and JP2003-169802A or an acoustic wave measurement apparatus such as a photoacoustic wave measurement apparatus disclosed in JP2013-202050A, JP2013-188465A, JP2013-180330A, JP2013-158435A, JP2013-154139A, or the like.

<<Acoustic Wave Probe>>

Figure 1:
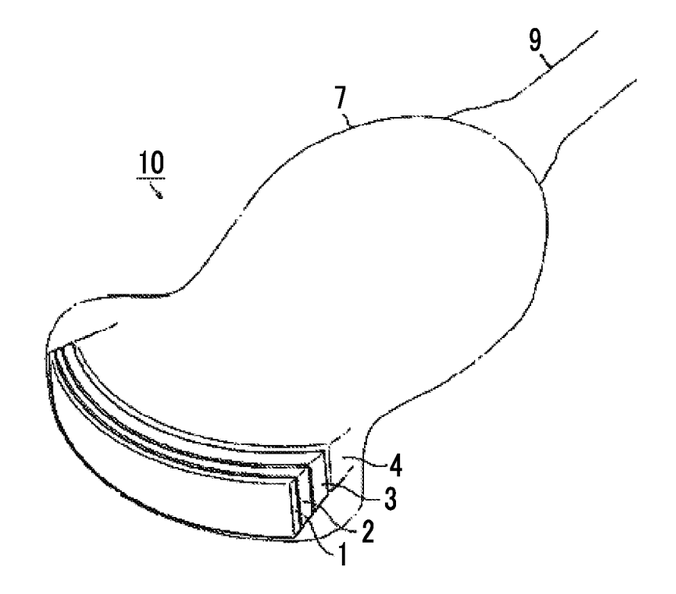
FIG. 1 is a perspective transparent view of an example of a convex ultrasound probe which is an aspect of an acoustic wave probe.

A configuration of an acoustic wave probe of the present invention will be described below in more detail based on a configuration of an ultrasound probe in an ultrasound diagnostic apparatus which is described in FIG. 1. The ultrasound probe is a probe which particularly uses an ultrasonic wave as an acoustic wave in an acoustic wave probe. For this reason, a basic configuration of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN, $Pb(Zr,Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

A composition for an ultrasound probe of the present invention can preferably be used as a material for the acoustic matching layer since the difference in acoustic impedance ($1.4 \times 10^6$ to $1.7 \times 10^6$ kg/m$^2$/sec) between the piezoelectric element layer and a living body is small.

The acoustic matching layer of the present invention preferably contains 10 mass % or more of a silicone resin for an acoustic wave probe obtained by subjecting the composition for an acoustic wave probe of the present invention to a crosslinking reaction.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.4 \times 10^6$ to $1.7 \times 10^6$ kg/m$^2$/sec in a case of a human body) of a living body which is a test object after being closely attached to the living body and to reduce ultrasonic attenuation of the acoustic lens 1 itself.

That is, sensitivity of transmission and reception of an ultrasonic wave is improved using a material of which the acoustic velocity is sufficiently lower than that of a human body, the ultrasound attenuation is low, and the acoustic impedance is close to a value of the skin of a human body, as the material of the acoustic lens 1.

The composition for an acoustic wave probe as a composition for an ultrasound probe of the present invention can also preferably be used as a material of the acoustic lens.

The operation of the ultrasound probe 10 having such a configuration will be described. The piezoelectric element layer 3 is resonated after applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the composition for an ultrasound probe of the present invention as a general medical ultrasonic transducer. Particularly, a remarkable effect of improving the sensitivity can be expected from a transmission frequency of an ultrasonic wave of greater than or equal to 10 MHz.

Hereinafter, an apparatus in which the acoustic lens obtained from the composition for an ultrasound probe of the present invention exhibits a function particularly regarding conventional problems will be described in detail.

The composition for an ultrasound probe of the present invention exhibits an excellent effect even with respect to other apparatuses disclosed below.

—Ultrasound Probe Including Capacitive Micromachined Ultrasonic Transducer (cMUT)—

In a case where cMUT apparatuses disclosed in JP2006-157320A, JP2011-71842A, and the like are used in an ultrasonic diagnostic transducer array, the sensitivity thereof generally becomes low compared to a transducer in which usual piezoelectric ceramics (PZT) is used.

However, it is possible to make up for deficient sensitivity of cMUT using the acoustic lens obtained from the composition for an acoustic wave probe of the present invention. Accordingly, it is possible to approximate the sensitivity of cMUT to performance of a conventional transducer.

The cMUT apparatus is manufactured through MEMS technology. Therefore, it is possible to provide an inexpensive ultrasound probe, of which mass productivity is higher than that of a piezoelectric ceramics probe, to the market.

—Photoacoustic Wave Measurement Apparatus Using Photo-Ultrasound Imaging—

Photoacoustic imaging (photo acoustic imaging: PAI) disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the composition for an acoustic wave probe of the present invention.

—Ultrasound Endoscope—

In an ultrasonic wave in an ultrasound endoscope disclosed in JP2008-311700A or the like, a signal line cable is structurally long compared to that of a transducer for a body surface, and therefore, there is a problem of improving the sensitivity of the transducer accompanied by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is a small installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity using piezoelectric single crystal material.

However, it is possible to improve the sensitivity of the endoscope ultrasonic transducer using the acoustic lens obtained from the composition for an acoustic wave probe of the present invention.

In addition, even in a case of using the same ultrasonic transmission frequency (for example, 10 MHz), the efficacy is particularly exhibited in a case of using the acoustic lens obtained from the composition for an acoustic wave probe of the present invention in the ultrasonic transducer for an endoscope.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

Example 1

55.0 parts by mass of a vinyl terminated diphenylsiloxane-dimethylsiloxane copolymer (a component (A) in Table 1 which was "PDV-0541" manufactured by GELEST, INC. with a mass average molecular weight of 60,000 and a diphenylsiloxane amount of 5 mol %) and 45.0 parts by mass of truly spherical surface-treated silica (a component (B) in Table 1 which was "QSG-30" manufactured by Shin-Etsu Chemical Co., Ltd. with an average primary particle diameter of 30 nm and a surface-treated product with methyltrimethoxysilane and hexamethyldisilazane (HMDS) and had a methanol hydrophobicity of 67 mass %), were kneaded with a 6-inch double roll kneader for 2 hours at a temperature of 23° C., and 0.5 parts by mass of 2,5-dimethyl-2,5-di-(t-butyl peroxy) hexane (a component (C) in Table 1 which was "PERHEXA 25B" manufactured by NOF CORPORATION) was subjected with roll mixing for 15 minutes at a temperature of 23° C. to prepare a molding compound. This molding compound was placed in a 100 mm×100 mm metal mold, subjected to press molding for 10 minutes at 165° C., and further subjected to secondary cross-linking for 2 hours at 200° C. to obtain a silicone resin sheet having a thickness of 2 mm.

Examples 2 to 16, 19, and 20 and Comparative Examples 2 and 5

Predetermined silicone resin sheets were produced similarly to Example 1 except that the composition of Example 1 was changed to the composition disclosed in Table 1.

Examples 17 and 18 and Comparative Examples 3 and 4

Truly spherical surface-treated silica particles B1, B2, T1, and T2 having an average primary particle diameter and a methanol hydrophobicity described in Table 1 were obtained through similar processing except that the amounts of methanol, water, and 28% aqueous ammonia in a step (A1) in the example disclosed in Synthesis Example 1 of JP2007-99582A were changed.

A predetermined silicone resin sheet was produced in the same manner as in Example 1 except that the obtained truly spherical surface-treated silica particles were used as the component (B).

Comparative Example 1

55.0 parts by mass of a vinyl terminated diphenylsiloxane-dimethylsiloxane copolymer ("PDV-0541" manufactured by GELEST, INC. with a mass average molecular weight of 60,000 and a diphenylsiloxane amount of 5 mol %) and 45.0 parts by mass of heteromorphic surface-treated fumed silica ("AEROSIL (registered trademark) R974" manufactured by NIPPON AEROSIL CO., LTD. with an average primary particle diameter of 12 nm which was a surface-treated product with dimethyldichlorosilane (DDS) and had a methanol hydrophobicity of 33 mass %) were kneaded with a kneader for 2 hours at a set temperature of 23° C. However, since the viscosity was too high, the kneader overloaded and stopped. Therefore, it was impossible to knead the mixture.

Comparative Example 6

55.0 parts by mass of a vinyl terminated diphenylsiloxane-dimethylsiloxane copolymer ("PDV-0541" manufactured by GELEST, INC. with a mass average molecular weight of 60,000 and a diphenylsiloxane amount of 5 mol %) and 45.0 parts by mass of heteromorphic non-treated fumed silica ("AEROSIL (registered trademark) 50" manufactured by NIPPON AEROSIL CO., LTD. with an average primary particle diameter of 30 nm without surface treatment which had a methanol hydrophobicity of 0 mass %) were kneaded with a kneader for 2 hours at a set temperature of 23° C. However, since the viscosity was too high, the kneader overloaded and stopped. Therefore, it was impossible to knead the mixture.

[Methanol Hydrophobicity]

50 ml of ion exchange water and 0.2 g of silica particles as samples were placed in a beaker at 25° C. and stirred with a magnetic stirrer, methanol was added dropwise thereto from a burette, and the amount (Xg) of methanol added dropwise until the whole sample settles was measured. The methanol hydrophobicity was calculated using the following equation.

Methanol hydrophobicity(mass %)=$X/(50+X)\times 100$

<Evaluation of Mechanical Strength and Ultrasonic Characteristics>

The following evaluation was performed on silicone resin sheets of Examples 1 to 20 and Comparative Examples 2 to 5. Since kneading could not be performed in Comparative Examples 1 and 6, no evaluation was performed.

[Hardness]

The type A durometer hardness of each of the obtained silicone resin sheets with a thickness of 2 mm was measured using a rubber hardness meter (trade name "RH-201A" manufactured by Excel co., Ltd.) in compliance with JIS K6253-3 (2012). In Table 1, the hardness is described as JIS hardness.

[Tear Strength]

A trouser-type test piece of a silicone resin sheet with a thickness of 2 mm was manufactured and the tear strength was measured in compliance with JIS K6252 (2007).

[IPA Swelling Degree]

The mass (A) of the obtained silicone resin sheet having a thickness of 2 mm and the mass (B) of the obtained silicone resin sheet after being immersed in isopropyl alcohol (IPA) at 23° C. for 48 hours were measured, and the degree of swelling (S [mass %]) was obtained using the following equation.

Swelling degree $[S]=(B-A)/A\times 100$

[Acoustic Impedance]

The density of each of the obtained silicone resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). The acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003) and acoustic impedance was obtained from a sum of the density and the acoustic velocity which had been measured.

[Acoustic (Ultrasonic) Attenuation and Acoustic (Ultrasonic) Sensitivity]

A sinusoidal signal (a wave) of 5 MHz which had been output from an ultrasound oscillator (a function generator with a trade name of "FG-350" manufactured by IWATSU ELECTRIC CO., LTD.) was input into an ultrasound probe (manufactured by JAPAN PROBE), and an ultrasound pulse wave with a center frequency of 5 MHz was generated in water from the ultrasound probe. The magnitude of the amplitude before and after the generated ultrasonic wave passed through each of the obtained silicone resin sheet with a thickness of 2 mm was measured in a water temperature environment of 25° C. using an ultrasound receiver (an oscilloscope with a trade name of "VP-5204A" manufactured by Matsushita Electric Industrial Co., Ltd.). The acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet. The higher the acoustic (ultrasonic) sensitivity is, the smaller the acoustic (ultrasonic) attenuation is.

$$\text{Acoustic(Ultrasonic)sensitivity} = 20 \times \text{Log}(Vs/Vin)$$

The obtained results were summarized and shown in Table 1.

In Table 1, the mass average molecular weight of the polysiloxane (component (A)) is simply described as a molecular weight, and the type of each component is indicated by a trade name.

TABLE 1

| | | | Example 1 | Example 2 | Example-3 | Example 4 | Example 5 | Example 6 |
|---|---|---|---|---|---|---|---|---|
| Mixed composition | Component (A) | Type | PDV-0541 | PDV-0535 | PDV-1641 | PDV-1635 | DMS-V52 | DMS-V46 |
| | | Molecular weight | 60,000 | 47,500 | 55,000 | 35,300 | 155,000 | 117,000 |
| | | Content [parts by mass] | 55.0 | 55.0 | 55.0 | 55.0 | 55.0 | 55.0 |
| | Component (B) | Type | QSG-30 | QSG-30 | QSG-30 | QSG-30 | QSG-30 | QSG-30 |
| | | Average primary particle diameter [nm] | 30 | 30 | 30 | 30 | 30 | 30 |
| | | Shape | True spherical shape | True spherical shape | True spherical shape | True spherical shape | True spherical shape | True spherical shape |
| | | MeOH hydrophobicity [mass %] | 67 | 67 | 67 | 67 | 67 | 67 |
| | | Content [parts by mass] | 45.0 | 45.0 | 45.0 | 45.0 | 45.0 | 45.0 |
| | Component (C) | Type | 25B | 25B | 25B | 25B | 25B | 25B |
| | | Content [parts by mass] | 0.5 | 0.5 | 0.5 | 0.5 | 0.5 | 0.5 |
| Evaluation | JIS hardness | | 43 | 46 | 41 | 39 | 40 | 42 |
| | Tear strength [N/cm] | | 42 | 28 | 13 | 11 | 72 | 56 |
| | IPA swelling degree [mass %] | | 6 | 5 | 5 | 4 | 8 | 7 |
| | Acoustic impedance [×10$^6$ kg/m$^2$/s] | | 1.40 | 1.40 | 1.52 | 1.52 | 1.28 | 1.28 |
| | Acoustic (ultrasonic) sensitivity [dB] | | −69.3 | −69.4 | −69.7 | −69.8 | −68.9 | −69.0 |

| | | | Example 7 | Example 8 | Exaple 9 | Example 10 |
|---|---|---|---|---|---|---|
| Mixed composition | Component (A) | Type | DMS-V41 | DMS-T72 | DMS-T63 | DMS-T61 |
| | | Molecular weight | 62,700 | 500,000 | 300,000 | 230,000 |
| | | Content [parts by mass] | 55.0 | 55.0 | 55.0 | 55.0 |
| | Component (B) | Type | QSG-30 | QSG-30 | QSG-30 | QSG-30 |
| | | Average primary particle diameter [nm] | 30 | 30 | 30 | 30 |
| | | Shape | True spherical shape | True spherical shape | True spherical shape | True spherical shape |
| | | MeOH hydrophobicity [mass %] | 67 | 67 | 67 | 67 |
| | | Content [parts by mass] | 45.0 | 45.0 | 45.0 | 45.0 |
| | Component (C) | Type | 25B | 25B | 25B | 25B |
| | | Content [parts by mass] | 0.5 | 0.5 | 0.5 | 0.5 |
| Evaluation | JIS hardness | | 45 | 23 | 25 | 29 |
| | Tear strength [N/cm] | | 45 | >100 | >100 | 81 |
| | IPA swelling degree [mass %] | | 6 | 9 | 8 | 8 |
| | Acoustic impedance [×10$^6$ kg/m$^2$/s] | | 1.28 | 1.27 | 1.27 | 1.27 |
| | Acoustic (ultrasonic) sensitivity [dB] | | −69.1 | −69.0 | −69.1 | −69.1 |

TABLE 2

| | | | Example 11 | Example 12 | Example 13 | Example 14 | Example 15 |
|---|---|---|---|---|---|---|---|
| Mixed composition | Component (A) | Type | DMS-T46 | DMS-T41 | PDV-0541 | PDV-0541 | PDV-0541 |
| | | Molecular weight | 115,000 | 60,000 | 60,000 | 60,000 | 60,000 |
| | | Content [parts by mass] | 55.0 | 55.0 | 55.0 | 55.0 | 55.0 |

TABLE 2-continued

|  |  |  |  |  |  |  |  |
|---|---|---|---|---|---|---|---|
|  | Component (B) | Type | QSG-30 | QSG-30 | QSG-80 | YA050C-SP3 | MSP-011 |
|  |  | Average primary particle diameter [nm] | 30 | 30 | 80 | 50 | 30 |
|  |  | Shape | True spherical shape | True spherical shape | True spherical shape | True spherical shape | Heteromorphic shape |
|  |  | MeOH hydrophobicity [mass %] | 67 | 67 | 67 | 47 | 41 |
|  |  | Content [parts by mass] | 45.0 | 45.0 | 45.0 | 45.0 | 45.0 |
|  | Component (C) | Type | 25B | 25B | 25B | 25B | 25B |
|  |  | Content [parts by mass] | 0.5 | 0.5 | 0.5 | 0.5 | 0.5 |
| Evaluation |  | JIS hardness | 34 | 37 | 42 | 41 | 48 |
|  |  | Tear strength [N/cm] | 62 | 53 | 13 | 26 | 24 |
|  |  | IPA swelling degree [mass %] | 7 | 7 | 8 | 7 | 7 |
|  |  | Acoustic impedance [×10$^6$ kg/m$^2$/s] | 1.27 | 1.27 | 1.40 | 1.40 | 1.41 |
|  |  | Acoustic (ultrascnic) sensitivity [dB] | −69.3 | −69.4 | −69.2 | −69.0 | −69.7 |

|  |  |  | Example 16 | Example 17 | Example 18 | Example 19 | Example 20 |
|---|---|---|---|---|---|---|---|
| Mixed composition | Component (A) | Type | PDV-0541 | PDV-0541 | PDV-0541 | PDV-0541 | PDV-0541 |
|  |  | Molecular weight | 60,000 | 60,000 | 60,000 | 60,000 | 60,000 |
|  |  | Content [parts by mass] | 55.0 | 55.0 | 55.0 | 55.0 | 55.0 |
|  | Component (B) | Type | NAX50 | B1 | B2 | QSG-30 | QSG-30 |
|  |  | Average primary particle diameter [nm] | 30 | 18 | 97 | 30 | 30 |
|  |  | Shape | Heteromorphic shape | True spherical shape | True spherical shape | True spherical shape | True spherical shape |
|  |  | MeOH hydrophobicity [mass %] | 28 | 61 | 76 | 67 | 67 |
|  |  | Content [parts by mass] | 45.0 | 45.0 | 45.0 | 45.0 | 45.0 |
|  | Component (C) | Type | 25B | 25B | 25B | PERCUMYL D | PERBUTYL Z |
|  |  | Content [parts by mass] | 0.5 | 0.5 | 0.5 | 0.5 | 0.5 |
| Evaluation |  | JIS hardness | 50 | 46 | 43 | 38 | 37 |
|  |  | Tear strength [N/cm] | 11 | 49 | 10 | 34 | 27 |
|  |  | IPA swelling degree [mass %] | 8 | 6 | 9 | 7 | 7 |
|  |  | Acoustic impedance [×10$^6$ kg/m$^2$/s] | 1.40 | 1.40 | 1.40 | 1.40 | 1.40 |
|  |  | Acoustic (ultrascnic) sensitivity [dB] | −69.9 | −69.8 | −69.8 | −69.4 | −69.2 |

TABLE 3

|  |  |  | Comparative Example 1 | Comparative Example 2 | Comparative Example 3 | Comparative Example 4 | Comparative Example 5 | Comparative Example 6 |
|---|---|---|---|---|---|---|---|---|
| Mixed composition | Component (A) | Type | PDV-0541 | PDV-0541 | PDV-0541 | PDV-0541 | PDV-0541 | PDV-0541 |
|  |  | Molecular weight | 60,000 | 60,000 | 60,000 | 60,000 | 60,000 | 60,000 |
|  |  | Content [parts by mass] | 55.0 | 70.0 | 55.0 | 55.0 | 55.0 | 55.0 |
|  | Component (B) | Type | R974 | R974 | T1 | T2 | QSG-100 | 50 |
|  |  | Average primary particle diameter [nm] | 12 | 12 | 16 | 104 | 110 | 30 |
|  |  | Shape | Heteromorphic shape | Heteromorphic shape | True spherical shape | True spherical shape | True spherical shape | Heteromorphic shape |
|  |  | MeOH hydrophobicity [mass %] | 33 | 33 | 59 | 70 | 67 | 0 |
|  |  | Content [parts by mass] | 45.0 | 30.0 | 45.0 | 45.0 | 45.0 | 45.0 |
|  | Component (C) | Type | — | 25B | 25B | 25B | 25B | — |
|  |  | Content [parts by mass] | — | 0.5 | 0.5 | 0.5 | 0.5 | — |

TABLE 3-continued

|  |  | Comparative Example 1 | Comparative Example 2 | Comparative Example 3 | Comparative Example 4 | Comparative Example 5 | Comparative Example 6 |
|---|---|---|---|---|---|---|---|
| Evaluation | JIS hardness | Kneading cannot be performed since viscosity is too high | 58 | 46 | 42 | 39 | Kneading cannot be performed since viscosity is too high |
|  | Tear strength [N/cm] |  | 41 | 52 | 7 | 5 |  |
|  | IPA swelling degree [mass %] |  | 12 | 6 | 9 | 9 |  |
|  | Acoustic impedance [×10$^6$ kg/m$^2$/s] |  | 1.23 | 1.40 | 1.40 | 1.40 |  |
|  | Acoustic (ultrasonic) sensitivity [dB] |  | −71.5 | −70.4 | −70.5 | −71.5 |  |

<Notes of Table>
[Polysiloxane (Component (A))]

PDV-0541: trade name, vinyl terminated diphenylsiloxane-dimethylsiloxane copolymer manufactured by GELEST, INC., mass average molecular weight of 60,000, diphenylsiloxane amount of 5 mol %

PDV-0535: trade name, vinyl terminated diphenylsiloxane-dimethylsiloxane copolymer manufactured by GELEST, INC., mass average molecular weight of 47,500, diphenylsiloxane amount of 5 mol %

PDV-1641: trade name, vinyl terminated diphenylsiloxane-dimethylsiloxane copolymer manufactured by GELEST, INC., mass average molecular weight of 55,000, diphenylsiloxane amount of 16 mol %

PDV-1635: trade name, vinyl terminated diphenylsiloxane-dimethylsiloxane copolymer manufactured by GELEST, INC., mass average molecular weight of 35,300, diphenylsiloxane amount of 16 mol %

DMS-V52: trade name, vinyl terminated polydimethylsiloxane manufactured by GELEST, INC., mass average molecular weight of 155,000

DMS-V46: trade name, vinyl terminated polydimethylsiloxane manufactured by GELEST, INC., mass average molecular weight of 117,000

DMS-V41: trade name, vinyl terminated polydimethylsiloxane manufactured by GELEST, INC., mass average molecular weight of 62,700

DMS-T63: trade name, polydimethylsiloxane containing no vinyl group, manufactured by GELEST, INC., mass average molecular weight of 300,000

DMS-T61: trade name, polydimethylsiloxane containing no vinyl group, manufactured by GELEST, INC., mass average molecular weight of 230,000

DMS-T46: trade name, polydimethylsiloxane containing no vinyl group, manufactured by GELEST, INC., mass average molecular weight of 115,000

DMS-T41: trade name, polydimethylsiloxane containing no vinyl group, manufactured by GELEST, INC., mass average molecular weight of 60,000

DMS-T72: trade name, polydimethylsiloxane containing no vinyl group, manufactured by GELEST, INC., mass average molecular weight of 500,000

[Surface-Treated Silica Particles (Component (B))]

True spherical shape: having Wardell's sphericity of 0.9 to 1

Heteromorphic shape: having Wardell's sphericity of less than 0.9

QSG-30: trade name manufactured by Shin-Etsu Chemical Co., Ltd., average primary particle diameter of 30 nm, surface-treated product with methyltrimethoxysilane (hereinafter, abbreviated as MTMS) and hexamethyldisilazane (hereinafter, abbreviated as HMDS), true spherical shape, methanol hydrophobicity of 67 mass %

QSG-80: trade name manufactured by Shin-Etsu Chemical Co., Ltd., average primary particle diameter of 80 nm, surface-treated product with MTMS and HMDS, true spherical shape, methanol hydrophobicity of 67 mass %

YA050C-SP3: trade name manufactured by Admatechs, average primary particle diameter of 50 nm, surface-treated product with phenyltrimethoxysilane, true spherical shape, methanol hydrophobicity of 47 mass %

MSP-011: trade name manufactured by TAYCA, average primary particle diameter of 30 nm, surface-treated product with MTMS and HMDS, heteromorphic shape, methanol hydrophobicity of 41 mass %

AEROSIL NAX50: trade name manufactured by NIPPON AEROSIL CO., LTD., average primary particle diameter of 30 nm, fumed silica, surface-treated product with HMDS, heteromorphic shape, methanol hydrophobicity of 28 mass %

AEROSIL R974: trade name manufactured by NIPPON AEROSIL CO., LTD., average primary particle diameter of 12 nm, surface-treated product with dimethyldichlorosilane, heteromorphic shape, methanol hydrophobicity of 33 mass %

QSG-100: trade name manufactured by Shin-Etsu Chemical Co., Ltd., average primary particle diameter of 110 nm, surface-treated product with MTMS and HMDS, true spherical shape, methanol hydrophobicity of 67 mass %

AEROSIL 50: trade name, manufactured by NIPPON AEROSIL CO., LTD., average primary particle diameter of 30 nm, no surface treatment, heteromorphic shape, methanol hydrophobicity of 0 mass %

[In Table 1, "AEROSIL" is omitted. Although AEROSIL 50 is not surface-treated, it is described in the row of component (B) for comparison with the examples.]

B1, B2, T1, T2: Silica particles synthesized above

">100 (Examples 8 and 9)" means that the tear strength is greater than 100 N/cm.

<Organic Peroxide (Component (C))>

25B: Manufactured by NOF CORPORATION, and a trade name "PERHEXA 25B" is simply described as "25 B".

PERCUMYL D: trade name manufactured by NOF CORPORATION, dicumyl peroxide

PERBUTYL Z: trade name, manufactured by NOF Corporation, t-butyl peroxybenzoate

"-" means that the component (C) is not used.

As is apparent from Table 1, all of the silicone resins for an acoustic wave probe of Examples 1 to 20 could obtain high resin hardness and tear strength and excellent acoustic impedance while maintaining the acoustic (ultrasonic) sensitivities greater than or equal to −70.0 dB. In addition, it can be seen that the chemical resistance is excellent since the IPA swelling degrees are low in all of Examples 1 to 20.

In contrast, the viscosity of the composition for an acoustic wave probe before cross-linking was high in Comparative Example 1 in which silica particles having an average primary particle diameter of 12 nm are used, and therefore, it was impossible to knead the composition. In addition, in Comparative Example 2 in which the content of silica particles with an average primary particle diameter of 12 nm was reduced, even though it was possible to knead the composition, it was impossible to disperse the silica particles. Therefore, the silicone resin for an acoustic wave probe had poor chemical resistance and acoustic sensitivity. In Comparative Example 3 in which silica particles having an average primary particle diameter of 16 nm are used, the acoustic sensitivity is not sufficient. In Comparative Examples 4 and 5 in which silica particles having an average primary particle diameter exceeding 100 nm were used, the tear strength was low and the acoustic sensitivity was poor. In Comparative Example 6 in which silica particles of which the average primary particle diameter was within the range of the present invention and which were not subjected to surface treatment were used, the viscosity of the composition for an acoustic wave probe before cross-linking was high, and therefore, it was impossible to knead the composition.

From the results, it can be seen that the composition for an acoustic wave probe of the present invention is useful for a medical member. In addition, it can be seen that the silicone resin for an acoustic wave probe of the present invention can also be suitably used in the acoustic lens and/or the acoustic matching layer of the acoustic wave probe, the acoustic wave measurement apparatus, and the ultrasound diagnostic apparatus. Particularly, the composition for an acoustic wave probe and the silicone resin for an acoustic wave probe can be suitably used in the ultrasound probe in which cMUT is used as an ultrasonic diagnostic transducer array, the photoacoustic wave measurement apparatus, and the ultrasound endoscope for the purpose of improving the sensitivity.

The present invention has been described using an embodiment thereof. However, it is considered that, unless otherwise specified, even the detailed description of the invention is not limited and is necessarily widely interpreted without departing from the gist and the range of the invention shown in the attached Claims.

EXPLANATION OF REFERENCES

1: acoustic lens
2: acoustic matching layer
3: piezoelectric element layer
4: backing material
7: housing
9: cord
10: ultrasound probe

What is claimed is:

1. A composition for an acoustic wave probe, comprising:
a polysiloxane mixture containing polysiloxane and silica particles of which an average primary particle diameter exceeds 16 nm and less than 100 nm and which are subjected to surface treatment; and
organic peroxide,
wherein said silica particles have a methanol hydrophobicity of 40 to 80%,
wherein the polysiloxane is represented by the following Formula (A1):

wherein, in Formula (A1), $R^{a1}$'s each independently represent a hydrogen atom, an alkyl group, a cycloalkyl group, an alkenyl group or an aryl group, and $R^{a2}$ and $R^{a3}$ each independently represent a hydrogen atom, an alkyl group, a cycloalkyl group, an alkenyl group, an aryl group, or $-O-Si(R^{a5})_2(R^{a4})$ in which $R^{a4}$ and $R^{a5}$ each independently represent a hydrogen atom, an alkyl group, a cycloalkyl group, an alkenyl group, or an aryl group, x1 and x2 each independently represent an integer of 1 or more, and a plurality of $R^{a1}$'s, a plurality of $R^{a2}$'s, a plurality of $R^{a3}$'s, and a plurality of $R^{a5}$'s may be the same as or different from each other, and in a case where there are a plurality of $R^{a4}$'s, the plurality of $R^{a4}$'s may be the same as or different from each other, and
wherein the polysiloxane has a phenyl group and the content of the phenyl group in the polysiloxane is 2 to 40 mol %.

2. The composition for an acoustic wave probe according to claim 1,
wherein 25 to 70 parts by mass of the silica particles subjected to surface treatment are contained in 100 parts by mass in total of the polysiloxane mixture.

3. The composition for an acoustic wave probe according to claim 1,
wherein the polysiloxane is vinyl group-containing polysiloxane.

4. The composition for an acoustic wave probe according to claim 1,
wherein the silica particles subjected to surface treatment are silica particles subjected to surface treatment using a silane compound.

5. The composition for an acoustic wave probe according to claim 1,
wherein the silica particles subjected to surface treatment are silica particles subjected to surface treatment using a trimethylsilylating agent.

6. The composition for an acoustic wave probe according to claim 1,
wherein a methanol hydrophobicity of the silica particles subjected to surface treatment is 50 to 80 mass %.

7. The composition for an acoustic wave probe according to claim 1,
wherein the silica particles subjected to surface treatment are truly spherical.

8. The composition for an acoustic wave probe according to claim 1, wherein a mass average molecular weight of the polysiloxane is 20,000 to 1,000,000.

9. The composition for an acoustic wave probe according to claim 1, wherein a mass average molecular weight of the polysiloxane is 40,000 to 300,000.

10. A silicone resin for an acoustic wave probe which is obtained by cross-linking the composition for an acoustic wave probe according to claim 1.

11. An acoustic wave probe comprising:
an acoustic lens containing the silicone resin for an acoustic wave probe according to claim 10; and/or an acoustic matching layer containing the silicone resin for an acoustic wave probe according to claim 10.

12. An acoustic wave measurement apparatus comprising: the acoustic wave probe according to claim 11.

13. An ultrasound diagnostic apparatus comprising: the acoustic wave probe according to claim 11.

14. An ultrasound probe comprising:
a capacitive micromachined ultrasonic transducer as an ultrasonic transducer array; and
an acoustic lens containing the silicone resin for an acoustic wave probe according to claim 10.

15. A photoacoustic wave measurement apparatus comprising:
an acoustic lens containing the silicone resin for an acoustic wave probe according to claim 10.

16. An ultrasound endoscope comprising:
an acoustic lens containing the silicone resin for an acoustic wave probe according to claim 10.

17. The composition for an acoustic wave prove according to claim 1, wherein a content of the organic peroxide is 0.1 to 15 parts by mass with respect to 100 parts by mass of the polysiloxane.

\* \* \* \* \*